United States Patent [19]

Osborn

[11] Patent Number: 5,409,495
[45] Date of Patent: Apr. 25, 1995

[54] APPARATUS FOR UNIFORMLY IMPLANTING A STENT

[75] Inventor: Kenneth L. Osborn, Mountain View, Calif.

[73] Assignee: Advanced Cardiovascular Systems, Inc., Santa Clara, Calif.

[21] Appl. No.: 111,173

[22] Filed: Aug. 24, 1993

[51] Int. Cl.⁶ ............................................. A61M 29/02
[52] U.S. Cl. ..................................... 606/108; 606/194; 604/101
[58] Field of Search ................ 606/108, 194, 195, 192, 606/198; 604/96, 101, 103

[56] References Cited

U.S. PATENT DOCUMENTS

| | | |
|---|---|---|
| 4,327,736 | 5/1982 | Wove .................................. 604/101 |
| 4,733,665 | 3/1988 | Palmaz . |
| 4,739,762 | 4/1988 | Palmaz . |
| 4,776,337 | 10/1988 | Palmaz . |
| 4,856,516 | 8/1989 | Hillstead . |
| 4,913,141 | 4/1990 | Hillstead . |
| 4,950,227 | 8/1990 | Savin et al. . |
| 5,019,085 | 5/1991 | Hillstead . |
| 5,064,435 | 11/1991 | Porter . |
| 5,102,417 | 4/1992 | Palmaz . |
| 5,108,416 | 4/1992 | Ryan et al. . |
| 5,116,318 | 5/1992 | Hillstead . |
| 5,122,154 | 6/1992 | Rhodes . |
| 5,133,732 | 7/1992 | Wiktor . |
| 5,147,377 | 9/1992 | Sahota .................................. 606/194 |
| 5,226,889 | 7/1993 | Sheiban . |
| 5,226,913 | 7/1993 | Pinchuk . |
| 5,242,452 | 9/1993 | Inoue . |

*Primary Examiner*—Michael H. Thaler
*Attorney, Agent, or Firm*—Fulwider Patton Lee & Utecht

[57] ABSTRACT

An improved system for uniformly implanting a stent in a body lumen comprising an intravascular catheter having an elongated catheter body and at least one inflation lumen contained therein, the catheter body including proximal and distal ends, a balloon near the distal end of the catheter for expanding the stent, an elastic sleeve surrounding and in contact with the balloon for controlling the radial expansion of the balloon and either restraining bands or a pair of control balloons to control the expansion of the balloon so that controllable expansion characteristics of the stent are achieved.

15 Claims, 3 Drawing Sheets

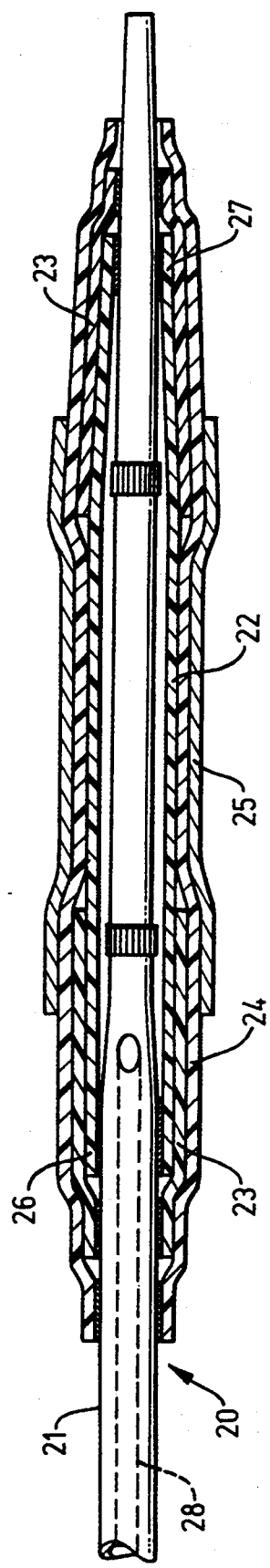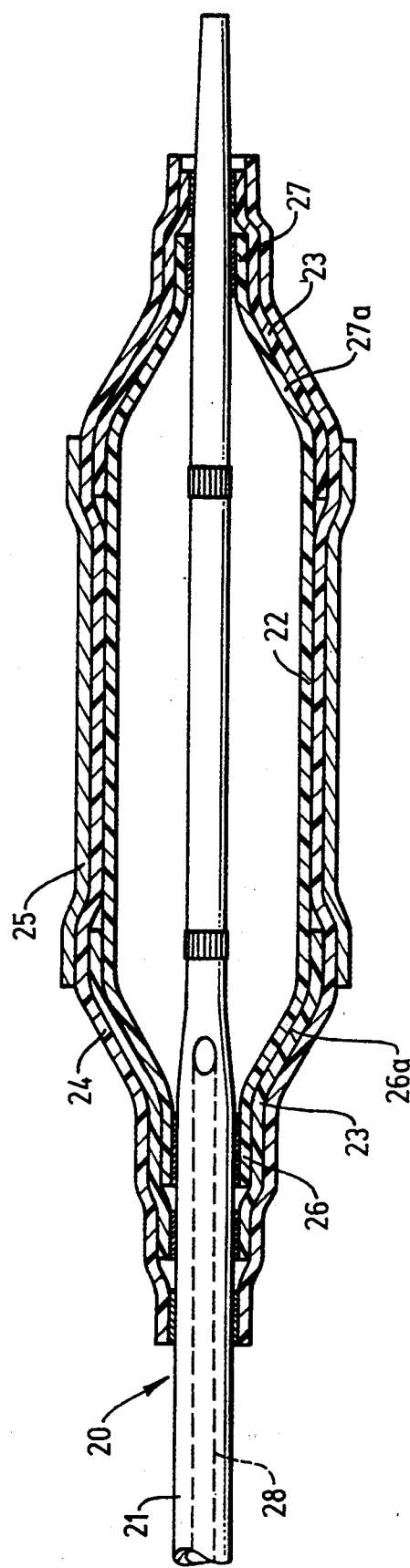

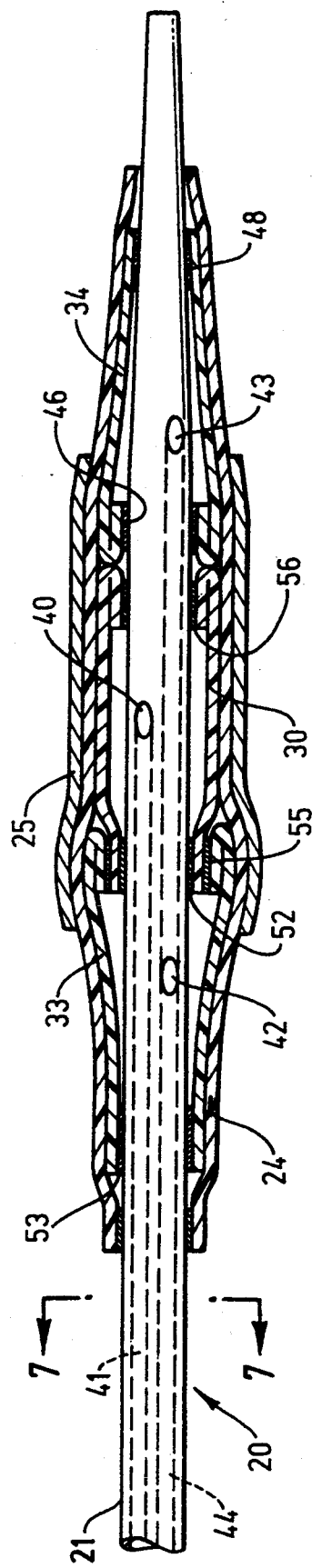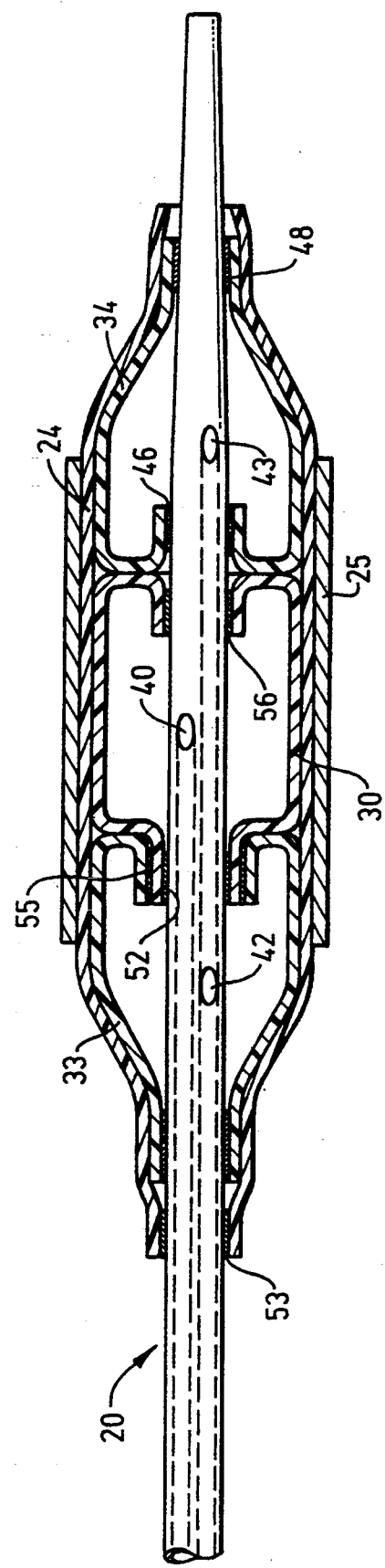

APPARATUS FOR UNIFORMLY IMPLANTING A STENT

BACKGROUND OF THE INVENTION

1. Field of the Invention

This invention relates generally to improvements in methods and apparatus for uniformly implanting a stent and, more particularly, to improved uniform stent implantation systems wherein radial expansion is controlled.

2. Description of Related Art

In typical percutaneous transluminal coronary angioplasty (PTCA) procedures, a guiding catheter is percutaneously introduced into the cardiovascular system of a patient through the brachial or femoral arteries and advanced through the patient's vasculature until the distal end of the guiding catheter is in the ostium of the desired coronary artery. A guidewire and a dilatation catheter having a balloon on the distal end of the dilatation catheter are introduced through the guiding catheter with the guidewire sliding within the dilatation catheter. First, the guidewire is passed through the guiding catheter and into the patient's coronary vasculature. Second, the dilatation catheter is advanced over the previously passed guidewire until the dilatation balloon is properly positioned across a lesion. Once in position across the lesion, a preformed balloon carried by the catheter is inflated to a predetermined size with a liquid at relatively high pressures (e.g., greater than about 4 atmospheres) to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. The PTCA procedure is also typically performed with the use of a guiding catheter, wherein a conventional over-the-wire system is employed.

In such angioplasty procedures, there may be restenosis of the artery, which necessitates either another angioplasty procedure, a surgical bypass operation, or some other method of repairing or strengthening the dilated area. To assist in the prevention of restenosis and to strengthen the dilated area, a physician can implant an intravascular prothesis, generally called a stent, to maintain vascular patency inside the artery at the site of the lesion. Stents are also used to repair vessels having a flap or dissection or to generally strengthen a weakened section of a vessel. The stent is expanded to a larger diameter, often by the balloon portion of the dilatation catheter. Stents delivered to a restricted coronary artery, expanded to a larger diameter by a balloon catheter, and left in place within the artery at the site of the dilated lesion are shown, for example, in U.S. Pat. No. 4,740,207 (Kreamer) and U.S. Pat. No. 5,007,926 (Derbyshire).

Although stents have been used effectively for some time, the effectiveness of a stent can be diminished if it is not uniformly implanted within the artery. For example, balloons having a stent placed upon them tend to have non-uniform radial expansion due to the increased restriction the stent imposes on the working length of the balloon. Consequently, the balloon expands first at the proximal and distal balloon ends along the path of least resistance, i.e., towards the distal and proximal ends of the balloon, which expands the balloon in a "dog bone" fashion lacking uniform radial expansion. Thus, when the balloon expands in this "dog bone" fashion, the proximal and distal regions of the balloon over expand to form a characteristic "dog bone" shape, the stent is not expanded uniformly and the stent may be improperly implanted.

Accordingly, those concerned with the design, development, and use of stent implantation systems have long recognized the desirability and need for further improvements in systems for uniformly implanting a stent in order to maximize stent performance. In this regard, what has been needed and, heretofore unavailable, is a stent delivery system which controls the radial expansion of the stent along its entire length to ensure uniform expansion.

SUMMARY OF THE INVENTION

Briefly, and in general terms, the present invention provides an improved method and apparatus for controlling the radial expansion of a catheter balloon used to deliver a stent, in order to enhance uniform implantation of the stent.

More particularly, the present invention comprises a catheter having first means on the catheter for expanding a stent, second means cooperating with the first means to control the radial expansion characteristics of the first means, and third means for controlling the radial expansion of the proximal and distal ends of the first means. In this way, the stent is more uniformly expanded to its implantation diameter and properly placed within the vasculature of a patient.

In one embodiment, by way of example and not necessarily by way of limitation, a balloon catheter includes an elongated catheter body and a balloon member on the distal end of the catheter. The balloon member has a proximal end and a distal end with each end having tapered balloon segments. Elastic restraining bands surround each of these distal and proximal tapered segments of the balloon. These restraining bands exert a resistive force in response to the resistive force created by the addition of the stent on the balloon. An uneven expansion is created in the balloon by the existence of the stent, thus the restraining bands help to offset this force. In order to further control the radial expansion of the balloon, a coaxial elastic sheath or sleeve surrounds and is in contact with the balloon member and the restraining bands. This results in only radial displacement along the entire length of the balloon. A stent, which is placed over the working length of the balloon, is therefore, uniformly expanded as the balloon is inflated, since radial expansion of the balloon is more precisely controlled.

During inflation of the balloon, the elastic restraining bands exert a force at the proximal and distal ends of the balloon equal and opposite to that generated by the combined resistance of the sleeve and the stent tending to deform the balloon. In this way, the uneven expansion (end effects) are limited when the balloon is expanded which, in turn, inhibits a "dog boning" deformation at the proximal and distal regions of the balloon. Further, as the balloon inflates, the sleeve surrounding the balloon distributes the radial forces evenly over an extended area, which then controls the radial expansion of both the balloon and the surrounding stent carried on the balloon.

In an another embodiment, a catheter includes an elongated catheter body and three balloons at the distal end of the catheter. The three balloons comprise a pair of control balloons and a central balloon located between the control balloons. In addition, a coaxial elastic sleeve surrounds all of the balloons and is in contact with the balloons.

In the latter catheter embodiment, the central balloon is formed of a conventional elastic material and is inflated to provide the primary expansion force, i.e., radial expansion to a stent which is placed upon the central balloon. It is noted, but not shown, that the stent may be placed over all three of the balloons.

The central balloon is the first of the three balloons to be inflated. As the central balloon inflates, it expands both radially and longitudinally. In order to control the longitudinal expansion, which occurs along the path of least resistance, the control balloons are formed of a material which is less compliant than the material forming the central balloon. One balloon of the pair is located proximally of the central balloon and the other balloon is located distally. Therefore, as the control balloons are inflated, they limit the longitudinal expansion of the central balloon by containing the central balloon between them.

Similarly, the elastic sleeve surrounding the three balloons controls the radial expansion of the central balloon. As discussed in the previous embodiment, the sleeve distributes the radial expansion forces generated by the central balloon over an extended area, thus, enabling the radial expansion of the balloon to remain more uniform.

Hence, by using the control balloons to contain the longitudinal expansion of the central balloon, and the elastic sleeve to control the radial expansion of the central balloon, the central balloon expands uniformly which, in turn, uniformly expands the stent from its smaller insertion diameter to its larger implantation diameter. This results in improved stent implantation which maximizes stent performance.

In another embodiment, the tri-balloon structure is again utilized, but without an elastic sleeve extending over the balloons to aid in distributing the radial expansion forces. In this embodiment, the control balloons again limit the longitudinal expansion of the elastic central balloon, and the central balloon, as the primary expansion balloon, expands radially upon inflation due to its elastic nature. Therefore, the control balloons not only limit the longitudinal expansion of the central balloon by containing the longitudinal expansion of the central balloon between them, but the control balloons also augment the radial expansion of the central balloon. Consequently, the expansion characteristics of the central balloon are controlled.

In still another embodiment, the tri-balloon structure is utilized either with or without the elastic sleeve covering the three balloons; however, in this embodiment, the central balloon is formed of a material having substantially similar elastic properties as the control balloons. Although the control balloons are no longer substantially less compliant than the central balloon, the control balloons still limit the longitudinal expansion of the central balloon during inflation as described above by containing the central balloon between them.

The present invention, in addition to implanting the stent, uniformly, reliably, rapidly, and precisely, also has numerous other advantages. The elastic sleeve, or the sleeve and restraining bands, are between the stent and the balloon member of the catheter. This prevents puncture of the balloon by any protuberance or other irregularity on the stent. This also prevents damage to the artery walls in the event the balloon develops a leak, which could enable high pressure fluid to escape through the leak, known as "pin-holing." In either case, the sleeve, with or without the restraining bands, forms a protective barrier which minimizes the harmful effects in the event the balloon is punctured or a pin-hole leak develops.

Further, the sleeve and restraining bands also provide a substrate for the stent, so that the stent may be secured to a balloon in a more positive manner. The sleeve, with or without the restraining bands, provides a cushion for the stent to sink into, and provides more friction for the stent than the slippery surface of the balloon which may be covered with an anti-friction material. Finally, the sleeve, with or without the restraining bands allows for a decrease in deflation time when the balloon is deflated, after the stent is implanted. The sleeve, with or without the restraining bands, reduces the deflation time by squeezing the balloon so it will deflate faster. Similarly, the sleeve and/or bands ensure that the balloon will deflate into a uniform, round balloon, and not into an undesirable flat or pancake shape, known as "balloon winging." Balloon winging is unacceptable because it increases the likelihood that the balloon will entangle when it is withdrawn from the stent and through the coronary arteries.

Other features and advantages of the present invention will become apparent from the following detailed description, taken in conjunction with the accompanying drawings, which illustrate, by way of example, the features of the present invention.

BRIEF DESCRIPTION OF THE DRAWINGS

FIG. 1 depicts a partial cross-sectional view of one embodiment of the present invention, illustrating a balloon catheter having an elastic sleeve and a plurality of elastic restraining bands outside the balloon member of the catheter, wherein the balloon is deflated;

FIG. 2 depicts a partial cross-sectional view of the balloon, the elastic sleeve and the elastic restraining bands of FIG. 1, wherein the balloon is inflated;

FIG. 3 depicts a partial cross-sectional view of another embodiment of the present invention, illustrating a tri-balloon catheter and an elastic sleeve surrounding the balloons, wherein the tri-balloon portion is deflated;

FIG. 4 depicts a partial cross-sectional view of the elastic sleeve and the three balloons of FIG. 3, wherein the tri-balloon catheter is inflated;

DETAILED DESCRIPTION OF THE PREFERRED EMBODIMENTS

Figure 5:
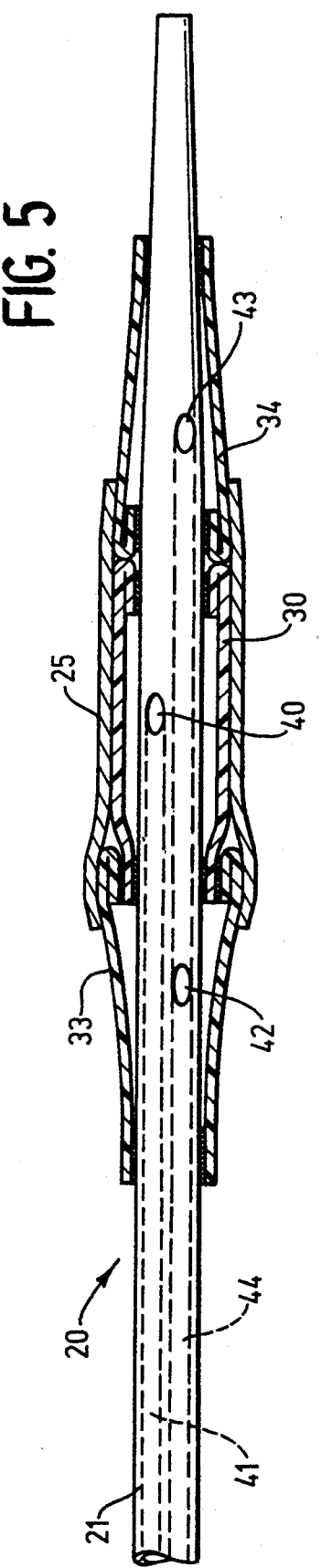
FIG. 5 depicts a partial cross-sectional view of another embodiment of the present invention, illustrating a tri-balloon catheter in its deflated state.

The present invention comprises a catheter having first balloon means for expanding a stent, cooperating with means for controlling the expansion characteristics of the balloon means. In this way, the stent is uniformly expanded to its implantation diameter and properly placed within the vasculature of a patient.

Referring now to the drawings, wherein like reference numbers denote like or corresponding elements throughout the various figures of the drawings, and more particularly to FIGS. 1 and 2, there is shown a catheter 20 embodying the novel features of the present invention. Catheter 20 includes a longitudinally extending outer tubular member 21 with an inflatable balloon member 22 near the distal end thereof, and an inflation lumen 28. The balloon 22 has a proximal end 26 and a distal end 27 with each end having tapered balloon segments 26a and 27a respectively. Elastic restraining bands 23 surround each of balloon segments 26a and 27a (FIG. 2). Restraining bands 23 are sealed to the outer tubular member 21 in any acceptable manner, as by way of standard adhesive techniques or via standard shrink tubing. In addition, an elastic sleeve 24 which is coaxial with the catheter, extends over the surface of balloon 22 and over restraining bands 23 and is in contact with both the balloon and the bands. A stent 25 is placed over sleeve 24 and positioned between restraining bands 23 or, alternatively, just slightly over the restraining bands.

In order to aid in the balloon's inflation, lubrication, such as MICROGLIDE TM coating (or a similar material), marketed by Advanced Cardiovascular Systems, Inc. (ACS) of Santa Clara, Calif., is placed between all the interfacing surfaces of restraining bands 23, balloon 22 and sleeve 24. This lubrication is used to offset the additional friction that is imparted by restraining bands 23 and sleeve 24 so that balloon 22 is still able to inflate without additional difficulty, i.e., the purpose of the restraining bands and the sleeve is to enhance the uniform expansion of the balloon, not to interfere with its inflation.

Balloon member 22 of catheter 20 is formed of polyethylene or other suitable materials well known in the art, and is either bonded to outer tubular member 21 in an integral manner, as shown, or is made one-piece with the outer member. Balloon 22 can be inflated by radiopaque fluid from an inflation port (not shown) extending from inflation lumen 28 contained in the catheter shaft, or by other means, such as fluid in communication from a passageway formed between the outside of the catheter shaft and the member forming the balloon, depending on the particular design of the catheter. The details and mechanics of balloon inflation vary according to the specific design of the catheter, and are well known in the art.

As stated above, sleeve 24 is coaxial with the catheter 20 and it surrounds both balloon 22 and restraining bands 23 which are located at proximal 26 and distal 27 ends of the balloon. The sleeve 24 has an inner diameter which is smaller than the outer diameter of balloon 22. Accordingly, sleeve 24 is attached to balloon 22 by stretching the sleeve over the balloon and restraining bands 23. In this way, compression is applied by sleeve 24 against balloon 22 and restraining bands 23 to form a secure seal. Sleeve 24 is also attached to the catheter outer tubular member 21 at proximal end 26 of balloon 22 via standard adhesive techniques or via standard shrink tube. Sleeve 24 is attached to proximal end 26 of balloon 22, because in the event of a rupture, the sleeve will be connected at the end upstream from the location of the tear and, thus, the sleeve will not curl or bunch when catheter 20 is withdrawn. The distal end of sleeve 24, however is not secured to the catheter outer tubular member 21 by adhesives. This allows for the translation of the sleeve during expansion and the passage of fluid distal to balloon 22 in the event of a balloon rupture.

Sleeve 24 may be formed of any suitable material that is elastic and resilient. The material is preferably one that has a high degree of linearity (non-plasticity) for a wide range of stress and strain values. However, any elastic material may be used. Commercially available tubing such as "C-FLEX" tubing may be used. "C-FLEX" tubing may be obtained from Concept Polymer Technologies of Largo, Florida. Further, the material should have good tear strength to prevent fracturing or splitting when it is stretched. Suitable materials include silicones, latexes, urethanes, polysiloxane modified styrene-ethylene/butylene-styrene block copolymers (SEBS) and their associated families.

While it is envisioned, in the embodiment of FIG. 1, that an elastic material is used to form sleeve 24 in order to maximize the benefits of the present invention, it is contemplated that other materials may be used, including materials such as the type used to form a balloon member of a PTCA catheter, like PE-600, a polyethylene based material marketed by Advanced Cardiovascular Systems, Inc. (ACS) of Santa Clara, Calif. Such materials are expandable, i.e., inflatable, but would not necessarily have to be resilient, as is the material contemplated in the embodiment shown in FIG. 1. Therefore, as is known in the art, materials that constitute the balloon members of PTCA catheters are expandable from one diameter to a larger predetermined diameter, being preformed to expand to the larger diameter, but are not necessarily elastic or resilient.

Similarly, elastic restraining bands 23 can be formed of the same material forming elastic sleeve 24. Alternatively, restraining bands 23 can be formed of a different material than that forming sleeve 24; however, the material chosen to form the restraining bands should have the similar elastic properties as that of the sleeve. Suitable materials for this purposes include "TYGON" available from U.S. Stoneware Co., or silicone.

As best observed in FIG. 2, when balloon 22 inflates, it expands radially. Restraining bands 23 control the expansion of balloon 22 by imparting a force which restricts the balloon's expansion at its proximal and distal ends, which is along the path of least resistance. Sleeve 24 also controls the radial expansion of balloon 22 by distributing the radial expansion of the balloon over an extended area. In other words, restraining bands 23 impart a resistance towards the proximal and distal ends of the balloon, equivalent to the combined resistance of sleeve 24 and stent 25. Thus, the radial expansion of balloon 22 is controlled to produce uniform expansion of the stent 25 from its smaller insertion diameter to its larger implantation diameter. This novel approach eliminates the "dog boning" affect that is common with prior art devices.

In an alternative embodiment, as shown in FIG. 3, a catheter 20 comprises three balloons 30, 33 and 34 near the distal end of the catheter, two inflation lumens 41 and 44, and an elastic sleeve 24 which is coaxial with the catheter and surrounds and is in contact with the three balloons. The three balloons 30, 33 and 34 include a pair of control balloons 33 and 34 formed of a non-compliant material, and a central balloon 30 which is located centrally between the control balloons. Control balloon 33 is located proximal to central balloon 30 and control balloon 34 is located distal to the central balloon.

Distal balloon 34 of the present invention is formed of a high pressure material, such as polyester. As shown in FIG. 4, distal balloon 34 is attached to outer tubular member 21 of catheter 20. A proximal seal 46 of distal balloon 34 is completed with the balloon 34 turned inside-out and the distal end laying towards the proximal end of outer tubular member 47. Once the proximal seal 46 is made, distal balloon 34 is folded back over the proximal seal so that distal seal 48 is formed using a standard tip seal technique as is well known in the art.

Proximal balloon 33 is similarly formed of a high pressure material. It is attached to the outer tubular member 21 in basically the reverse order as the procedure used to attach distal balloon 34. Proximal balloon 33 is turned inside-out, but this time with the proximal end of balloon 50 laying towards the distal end of outer tubular member 51. Distal seal 52 is then completed at the same time as the proximal seal 55 of the central balloon 30. Finally, proximal balloon 33 is folded back towards its proximal end 50 and proximal seal 53 is formed using a standard proximal seal technique as is well known in the art.

Central balloon 30 is formed of a compliant material, such as polyethylene. Generally, the entire stent 25 will be placed over central balloon 30, however, the stent may be placed over proximal and distal balloons 33 and 34, so long as these balloons also have a suitable working surface. Like proximal balloon 33 above, central balloon 30 is attached to outer tubular member 21 of catheter 20 turning it inside-out, with proximal end 31 of the central balloon laying towards the distal end of outer tubular member 51 to form distal seal 56. Then, central balloon 30 is folded back over itself and proximal seal 55 is formed, as stated above, at the same time distal seal 52 of the proximal balloon 33 is formed.

Coaxial elastic sleeve 24 is formed of "C-FLEX" or other similar elastic material and it surrounds and is in contact with balloons 30, 33 and 34. Sleeve 24 has an inner diameter which is smaller than the outer diameter of balloons 30, 33 and 34. Therefore, sleeve 24 is attached to balloons 30, 33 and 34 by stretching and placing the sleeve over all three balloons to form a secure seal. A stent 25 is placed over sleeve 24, typically, in the region overlying central balloon 30. As central balloon 30 inflates to provide radial expansion, sleeve 24 distributes the radial expansion force over an extended area, thus making the radial expansion uniform. This in turn allows stent 25 to be expanded uniformly for proper implantation.

Figure 6:
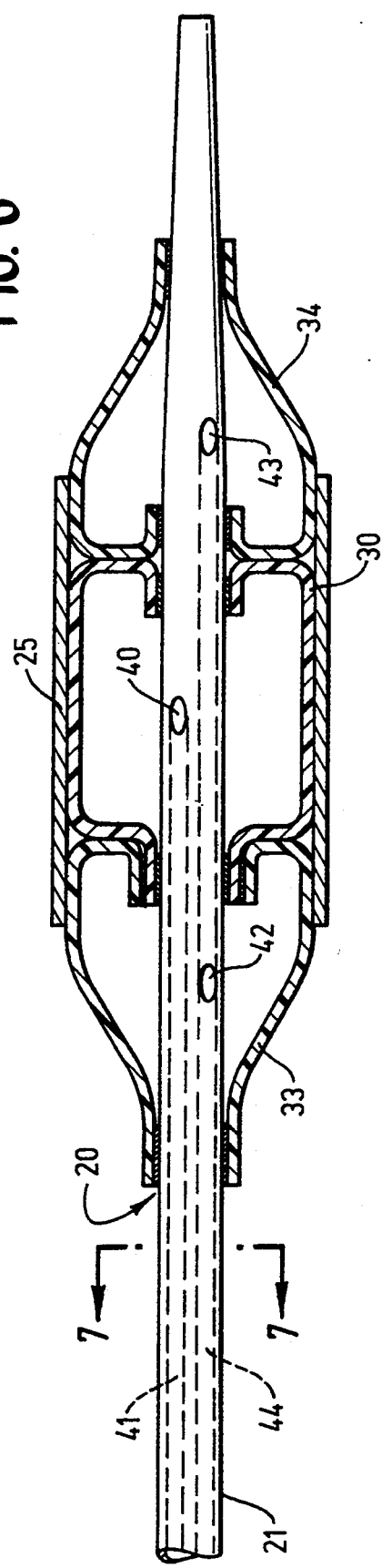
FIG. 6 depicts a partial cross-sectional view of the tri-balloon catheter of FIG. 5, showing all three of the balloons, in their inflated state.
Figure 7:
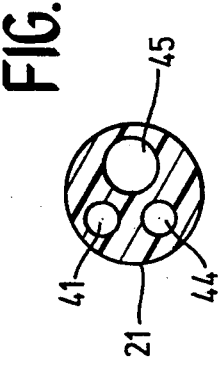
FIG. 7 is a transverse cross-sectional view taken substantially along lines 7—7 of the catheter shown in FIG. 6.

Central balloon 30 is the first of balloons 30, 33 and 34 to be inflated and provides the primary radial expansion force necessary to expand the stent 25 to its larger implantation diameter. Inflation of central balloon 30 is accomplished through the use of an inflation medium from inflation port 40 extending from first inflation lumen 41 contained in catheter shaft 21. After central balloon 30 has been inflated, proximal and distal balloons 33 and 34 are inflated via inflation medium from two additional inflation ports 42 and 43 which extend from a common second inflation lumen 44 contained in catheter shaft 21. In FIG. 7, a transverse cross-sectional view of the catheter shown in FIG. 6 illustrates the configuration of inflation lumens 41 and 44 along with wire lumen 45.

Therefore, catheter 20 is inserted into a patient's vasculature and central balloon 30 is inflated to produce both radial and longitudinal expansion of the balloon. Next, proximal balloon 33 and distal balloon 34 are inflated. Because of their less compliant construction, proximal and distal balloons 33 and 34 contain the central balloon 30 between them and, thus, limit the longitudinal expansion of the central balloon. Likewise, sleeve 24 controls the radial expansion of the balloon 30, which, in turn, controls the radial expansion of stent 25.

In still another embodiment, as illustrated in FIG. 5, the tri-balloon catheter of FIG. 4 can be used without a coaxial elastic sleeve 24 surrounding balloons 30, 33 and 34. Except for the absence of sleeve 24, the tri-balloon catheter 20 of this embodiment comprises the same structure and is constructed in the same manner as the tri-balloon catheter previously described in connection with the structure shown in FIG. 4.

As discussed in the aforedescribed embodiment, as central balloon 30 inflates, it provides radial expansion forces in order to implant stent 25. As central balloon 30 inflates it also expands longitudinally, along the path of least resistance. By inflating proximal and distal balloons 33 and 34, the longitudinal expansion of the central balloon 30 is restricted. In turn, the uniform radial expansion of central balloon 30 is enhanced. This in turn results in a more uniform expansion of stent 25 which aids in the uniform implantation of the stent.

In still another embodiment, the tri-balloon catheter 20 is utilized either with or without elastic sleeve 24; however, in this embodiment, balloons 30, 33 and 34 are formed of materials having substantially similar elastic properties. Therefore, control balloons 33 and 34 are not necessary less compliant than central balloon 30. Nevertheless, the catheter of this embodiment performs in substantially the same way as previously described. The central balloon 30 is inflated first to provide the primary radial expansion force necessary to implant stent 25. Subsequently, control balloons 33 and 34 are inflated to restrict the longitudinal expansion of central balloon 30. Although control balloons 33 and 34 are not less compliant than central balloon 30, they still provide adequate containment of the central balloon to restrict the longitudinal expansion of the central balloon. Once again, this allows for controlled expansion of stent 25 and more uniform implantation in the patient's vasculature.

It is clear from the above descriptions, that the present invention fulfills a long felt need for a system which can uniformly implant a stent in the vasculature of a patient. By controlling the uniform radial expansion of a balloon, a more uniform implantation of the stent is accomplished.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. In an intravascular catheter system for implanting a stent in a body lumen, the combination comprising:
   a catheter having an elongated catheter body and at least one inflation lumen contained therein, said catheter body having proximal and distal ends;
   a stent carried upon said catheter;
   a balloon attached to said catheter body near said distal end for controllably expanding said stent which is mounted thereon, said balloon in fluid communication with said inflation lumen to expand said balloon radially and longitudinally;
   an elastic sleeve coaxial with and surrounding said catheter body to control the radial expansion of said balloon; and
   an elastic restraining band positioned at each of the distal and proximal ends of said balloon to control longitudinal expansion of said balloon, whereby said stent mounted on said balloon is similarly controlled in its radial and longitudinal expansion to provide a cylindrically shaped stent implanted within the body lumen.

2. In an intravascular catheter system for implanting a stent in a body lumen, the combination comprising:
a catheter having an elongated catheter body and at least one inflation lumen contained therein, said catheter body having proximal and distal ends;
a stent carried upon said catheter;
a balloon having a proximal and distal end, said balloon attached to said catheter body near said distal end for controllably expanding said stent which is mounted thereon, said balloon in fluid communication with said inflation lumen to expand said balloon radially and longitudinally; and
an elastic sleeve and a plurality of elastic restraining bands, said sleeve and said bands surrounding said balloon for controlling the radial expansion of said balloon, said sleeve and said bands limiting the radial expansion of said balloon, whereby said stent mounted on said balloon is similarly limited in its radial expansion to provide a cylindrically shaped stent implanted within the body lumen.

3. A catheter as set forth in claim 2, wherein said balloon has proximal and distal tapers and said elastic restraining bands are located over said proximal and distal tapers of said balloon, whereby said restraining bands substantially restrict said proximal and distal ends of said balloon along the axis of said catheter.

4. A catheter as set forth in claim 2, wherein said elastic sleeve is coaxial with said catheter and surrounds said balloon and said restraining bands, said sleeve being in contact with said balloon and said bands, and said sleeve distributes the radial expansion forces of said balloon over an extended area to provide for uniform radial expansion of said balloon, whereby uniform radial expansion of said stent is accomplished.

5. A catheter as set forth in claim 2, wherein said elastic sleeve and said elastic restraining bands have substantially the same elastic properties.

6. In an intravascular catheter system for implanting a stent in a body lumen, the combination comprising:
a catheter having an elongated catheter body and at least one inflation lumen contained therein, said catheter body having proximal and distal ends;
a stent carried upon said catheter;
a balloon having both a proximal end and a distal end, said balloon attached to said catheter body near said distal end for controllably expanding said stent which is mounted thereon, said balloon having a proximal and a distal end, and said balloon in fluid communication with said inflation lumen to expand said balloon radially and longitudinally;
an elastic sleeve surrounding and cooperating with said balloon to control the radial expansion of said balloon; and
a plurality of elastic restraining bands surrounding and cooperating with said balloon and said elastic sleeve for limiting longitudinal expansion of the proximal and distal ends of said balloon, whereby said stent mounted on said balloon is similarly limited in its radial expansion to provide a cylindrically shaped stent implanted within the body lumen.

7. A catheter as set forth in claim 6, wherein said balloon has proximal and distal tapers, and said elastic restraining bands are located over said proximal and distal tapers of said balloon, whereby said restraining bands restrict expansion of said proximal and distal ends of said balloon along the axis of said catheter.

8. A catheter as set forth in claim 7, wherein said elastic sleeve is coaxial with said catheter and surrounds said balloon and said restraining bands, said sleeve being in contact with said balloon and said bands, and said sleeve distributes the radial expansion forces of said balloon over an extended area to provide more uniform radial expansion of said balloon, whereby uniform radial expansion of said stent is accomplished.

9. A catheter as set forth in claim 6, wherein said elastic sleeve and said elastic restraining bands have the same elastic properties.

10. A catheter as set forth in claim 9, wherein said sleeve and said bands are fabricated of silicone.

11. A catheter as set forth in claim 9, wherein said sleeve and said bands are fabricated of latex.

12. A catheter as set forth in claim 9, wherein said sleeve and said bands are fabricated of urethane.

13. A catheter as set forth in claim 9, wherein said sleeve and said bands are fabricated of a polysiloxane modified styrene-ethylene/butylene-styrene block copolymer (SEBS).

14. In an intravascular catheter system for implanting a stent in a body lumen, the combination comprising:
a catheter having an elongated catheter body and at least one inflation lumen contained therein, said catheter body having proximal and distal ends;
a stent carried upon said catheter;
a central balloon having both a proximal end and a distal end, said central balloon attached to said catheter body near said distal end for controllably expanding said stent which is mounted thereon, said central balloon in fluid communication with said inflation lumen to expand said central balloon radially and longitudinally;
a pair of control balloons, said control balloons surrounding and cooperating with said central balloon for limiting longitudinal expansion of the proximal and distal ends of said central balloon, said control balloons in fluid communication with a second inflation lumen;
said central balloon being located between said control balloons, wherein one balloon of said pair of control balloons is located adjacent the proximal end of said central balloon and said other balloon of said pair is located adjacent the distal end of said central balloon;
said control balloons comprising a material substantially less compliant than said central balloon; and
said control balloons are inflated to limit longitudinal expansion of said central balloon as said central balloon is inflated, so both longitudinal and radial expansion is controlled, whereby said stent mounted on said central balloon is similarly limited in its longitudinal expansion to provide a cylindrically shaped stent implanted within the body lumen.

15. In an intravascular catheter system for implanting a stent in a body lumen, the combination comprising:
a catheter having an elongated catheter body and at least one inflation lumen contained therein, said catheter body having proximal and distal ends;
a stent carried upon said catheter;
a central balloon attached to said catheter body near said distal end for controllably expanding said stent which is mounted thereon, said central balloon in fluid communication with a first inflation lumen for expanding said central balloon radially and longitudinally;

a pair of control balloons attached to said catheter body near said distal end to control longitudinal expansion of said central balloon, said control balloons comprising a material substantially less compliant than said central balloon, said central balloon being located between said control balloons, said control balloons in fluid communication with a second inflation lumen to expand said balloons; and an elastic sleeve coaxial with said catheter body and surrounding at least said central balloon to control radial expansion of said central balloon, whereby said stent mounted on said central balloon is similarly controlled in its radial and longitudinal expansion to provide a cylindrically shaped stent implanted within the body lumen.

* * * * *